United States Patent [19]

Glikberg et al.

[11] Patent Number: 4,602,498
[45] Date of Patent: Jul. 29, 1986

[54] DENSITOMETER

[75] Inventors: Santiago Glikberg; Yizhak Marcus, both of Jerusalem, Israel

[73] Assignee: Yissum Research Development Company of the Hebrew University of Jerusalem, Jerusalem, Israel

[21] Appl. No.: 720,783

[22] Filed: Apr. 8, 1985

[30] Foreign Application Priority Data

Apr. 10, 1984 [IL] Israel ................................... 71488

[51] Int. Cl.$^4$ ............................................. G01N 9/00
[52] U.S. Cl. .................................................. 73/32 A
[58] Field of Search ............. 73/30, 32 A, 1 G, 1 DV

[56] References Cited

U.S. PATENT DOCUMENTS

| 2,713,788 | 7/1955 | Gott | 73/30 |
| 3,233,461 | 2/1966 | Heckl et al. | 73/30 |
| 3,728,893 | 4/1973 | Janssen | 73/32 |
| 4,170,894 | 10/1979 | Zupanick | 73/30 |
| 4,262,523 | 4/1981 | Stansfeld | 73/30 |
| 4,489,592 | 12/1984 | Pacanowski et al. | 73/1 G |

Primary Examiner—Stewart J. Levy
Assistant Examiner—Robert R. Raevis
Attorney, Agent, or Firm—Millen & White

[57] ABSTRACT

There is provided a pressurized flow densitometer for the determination of the PVT properties of fluids. The densitometer comprises a tube flown through by the fluid to be tested, an exciter and sensor means for causing said fluid-filled tube to vibrate and for sensing the frequency and amplitude of vibrations thus induced, a frequency meter for processing the output of the sensor means, a thermostat for maintaining the tube and the fluid at a selectable, constant temperature, a pump connected to, and arranged upstream of, the tube for moving the fluid through the tube at controllable rates of delivery. The densitometer further comprises a flow resistance connectable to, and arranged downstream of, the tube to pressurize the fluid in dependence on the rates of delivery, at least one fluid-containing bottle attachable to the suction line of the pump, and a bypass valve arranged between the tube and the flow resistance, whereby flushing of the tube is accomplishable by opening the bypass valve to the atmosphere.

6 Claims, 1 Drawing Figure

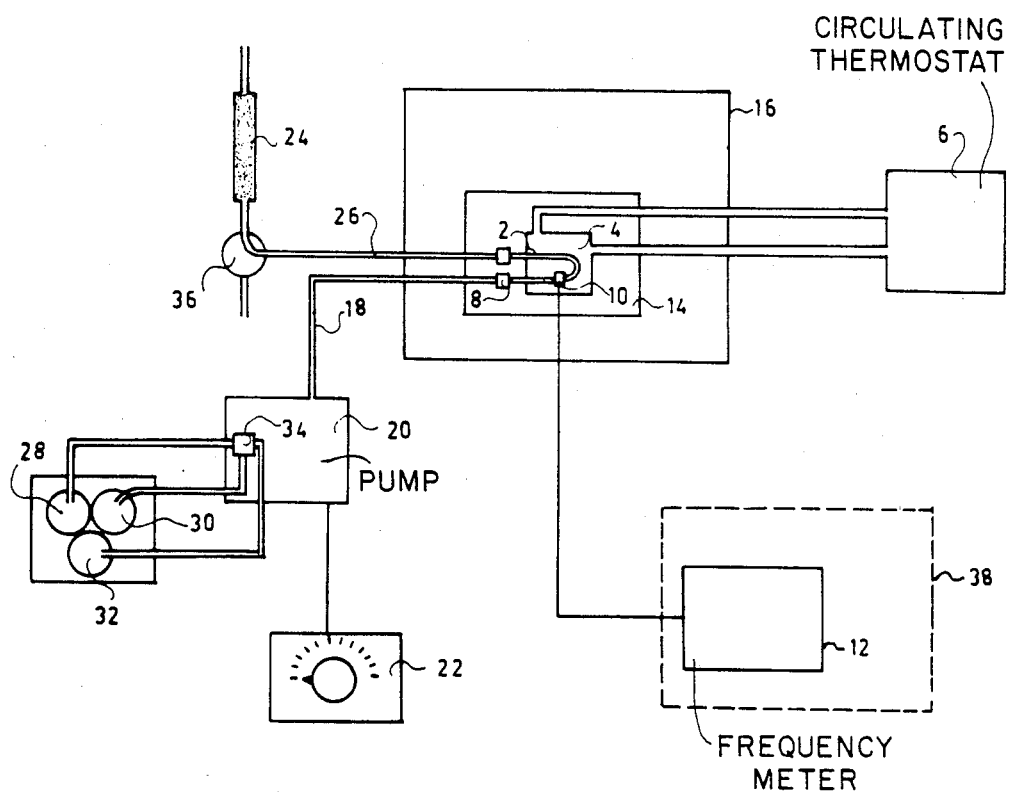

DENSITOMETER

The present invention relates to a pressurized flow densitometer for the determination of the PVT (pressure-volume-temperature) properties of fluids.

The properties of fluids, their mixtures and solutions depend on the temperature and the pressure to which they are subjected. The mathematical relationship between the applied pressure, the temperature and the resulting volume of a fluid is known as its equation of state. Since the theoretical form of this equation cannot be calculated for most fluids of practical industrial importance, empirical expressions have to be used. Those are based on the actual measurement of the PVT properties of the fluid.

The importance of the equation of state of a pure fluid or a solution resides in the fact that all the thermodynamic properties of the fluid can be deduced from it. These properties relate directly to the operative conditions of industrial processes, and to the structural changes occurring in the fluid under varying conditions. They are thus of paramount importance both to the chemical engineer and to the chemical researcher. Derivative quantities of the empirical equation of state are involved in the equation of the thermodynamic quantities. Hence, inaccuracies in the measurement of the PVT properties are greatly amplified. It is thus important to have an accurate method of measurement.

All methods of measurement of PVT properties of fluid consists in the measurement of either the volume or the density of the fluid over a range of temperatures and pressures. The only exeption is the one based on the measurement of ultrasound speed in the fluid. However, this method produces adiabatic thermodynamic quantities which are not directly useful to the chemical industry unless transformed by means of auxiliary data that are generally not readily available. The other methods are all adaptations of a technology in use at atmospheric pressure to higher pressures.

Among the methods commonly in use are the dilatometric, piezometric, volumometric, magnetic-float and direct weighing methods. The first three measure the volume ratio of the liquids between applied and atmospheric pressure at the selected temperature. The result is a relative measure of a volume change. The other two methods relate to density instead, and provide an absolute measure of it.

The most common method of measurement of PVT properties of liquids is the volumetric method which measures electrically the displacement of a piston or a bellows. Instruments using the magnetic-float method measure the current necessary to keep in equilibrium a magnetic float submerged in the liquid.

Instruments based on any of these methods are cumbersome to operate and have to be disassembled for changing from one liquid to another. They also require relatively long equilibration times.

It is one of the objects of the present invention to overcome the disadvantages and drawbacks of prior-art instrumentation used for determination of PVT properties, and to provide a device that, while comparable in accuracy with the best of the prior-art devices, is much simpler to operate, is merely flushed for change of liquids, and has substantially shorter equilibration times. It is also better suited to computerization and automation than any of the known PVT instruments.

This the invention achieves by providing a pressurized flow densitometer for the determination of the PVT properties of fluids, comprising:

a tube flown through by the fluid to be tested;

exciter and sensor means for causing said fluid-filled tube to vibrate and for sensing the frequency and amplitude of vibrations thus induced;

a frequency meter for processing the output of said sensor means;

a thermostat for maintaining said tube and said fluid at a selectable, constant temperature;

a pump connected to, and arranged upstream of, said tube for moving said fluid through said tube at controllable rates of delivery;

a flow resistance connectable to, and arranged downstream of, said tube to pressurize said fluid in dependence on said rates of delivery, and at least one fluid-containing bottle attachable to the suction line of said pump, further comprising a bypass valve arranged between said tube and said flow resistance, whereby flushing of said tube is accomplishable by opening said bypass valve to the atmosphere.

The invention will now be described in connection with a certain preferred embodiment with reference to the following illustrative FIGURE so that it may be more fully understood.

With specific reference now to the FIGURE in detail, it is stressed that the particulars shown are by way of example and for purposes of illustrative discussion of the preferred embodiment of the present invention only and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawing making apparent to those skilled in the art how the invention may be embodied in practice.

Referring now to the drawing which is a schematic representation of the device according to the invention, there is seen a U-shaped measurement tube 2 mounted in a cell 4 connected with a circulating thermostat 6 which can be set to any of the temperatures within the range of interest for the PVT properties and has a sensitivity of the order of 0.002°–0.003° C. The measuring tube 2 which must withstand pressures of up to 300 atm and must be inert with respect to as many liquids as possible, is made of stainless steel and is provided with high-pressure fittings 8 for connection with the rest of the device, as will be explained further below.

As the device according to the invention is based on the general relationship $\rho = f(\tau)$, where $\rho$ is the density of a liquid flowing through a tube and $\tau$ is the period of this tube when vibrating at resonant frequency, there is provided an oscillator-fed exciter 10 which causes the tube to vibrate through a spectrum of frequencies. A feed-back arrangement permits the exciter 10 also to function as sensor which produces an output signal that is fed to the recording frequency meter 12. This signal reaches a peak value when the frequency of the induced vibrations comes to coincide with the resonant frequency of the system: tube/liquid. The cell 2 is surrounded by insulative material 14 and placed in a thermostated box 16.

Liquid is supplied to the tube 2 via an inlet line 18 by means of a pump 20 the delivery rate of which is controllable from an electronic control unit 22. Pressure— one of the parameters of the PVT properties—is produced by a flow resistance 24 at the end of the outlet line 26. The flow resistance is constituted by, e.g., a stainless-steel tube filled with silica powder of a particle size of about 20 microns. In such arrangements, pressure is determined by the pump delivery rate, low pressures being produced by low rates, high pressures by high rates. The scale on the control unit 22 which, as already mentioned, controls in fact the rate of delivery of the pump (in this particular embodiment between 0.1 and 10 ml/min), is thus advantageously calibrated in units of pressure. The pump 20 itself must be of the nonpulsating type and has a minimum accuracy of about 1% of the rate as set.

The pump 20 draws liquid from bottles of which, in the embodiment described, there are three: vessel or bottle 28 which contains the liquid the PVT properties of which are to be measured and bottles 30 and 32 which carry each a liquid of known PVT properties, for a purpose to be explained further below. A selector valve 34, settable by the user, determines which of the three liquids is to be introduced into the measurement tube 2. Further provided is a two-way or by pass valve 36 by means of which flow from the outlet line 26 can be directed either to the flow resistance 24 or to the atmosphere. To reduce the effects of stray fields and noise on the frequency meter 12, the latter is advantageously enclosed in a Faraday cage 38.

The operational procedure is as follows: First, a temperature is selected in the circulating thermostat 6. After an adequate equilibration time, the maximum pressure in the desired range is selected on the control unit 22, the bypass valve 36 is set to establish a connection between the output line 26 and the flow resistance 24, and the system is left to operate at this pressure for 2–3 minutes. Then measurements are taken by the frequency meter and are averaged. Flow is stopped to select the next lower pressure, the bypass valve 36 is opened and closed again, and the device is now operated at the new pressure. This process is repeated until the entire pressure range is exhausted. After this, a new temperature is set and the entire process gone through again until the entire temperature range has been passed through. In order to change from one measuring liquid to another, all one has to do is to flush the system with the new liquid by operating the device for about 5–10 minutes with the bypass valve 36 open.

The precise form of the relationship between density $\rho$ and the period $\tau$ of vibration of tube 2 at resonant frequency, is $$\rho = A + B\rho^2,$$

where A and B are temperature- and pressure-dependent calibration constants which must be determined from time to time. This is easily done by using two liquids the PVT properties of which are fully known. Yet small drifts in the constants are also liable to occur between calibration measurement. To counteract such small drifts, each measurement of a liquid is accompanied by the measurement of a control liquid of known PVT properties, which facilitates calculation of a correction factor. The bottles 30 and 32 are in fact intended to contain such calibration and/or control liquids.

It will be appreciated that while the selector valve 34 constitutes a great convenience, it is not absolutely necessary. Since the pump 20 draws liquid only from one of the bottles 28, 30, 32 at a time, a single suction line leading to the pump 20 could be connected first to the bottle containing the first calibration liquid, then to the bottle for the second calibration liquid (in order to determine the calibration constants A and B), and then to the bottle containing the liquid to be tested for its PVT properties.

The temperature range achievable with the aid of the circulating thermostat 6 depends of course on the working liquid used. With water, the range would extend from near zero to about 95° C. Suitable liquids are available also for subzero temperatures as well as for temperatures above the boiling point of water.

For measurement at atmospheric pressure, the device is operated without the pump 20, and with the bypass valve 36 in the open position.

It will be evident to those skilled in the art that the invention is not limited to the details of the foregiong illustrative embodiments and example and that the present invention may be embodied in other specific forms without departing from the essential attributes thereof, and it is therefore desired that the present embodiments and example be considered in all respects as illustrative and not restrictive, reference being made to the appended claims, rather than to the foregoing description, and all changes which come with the meaning and range of equivalency of the claims are therefore intended to be embraced therein.

What is claimed is:

1. A pressurized flow densitometer for the determination of the PVT properties of fluids, comprising:
   a tube through which the fluid to be tested flows;
   exciter and sensor means for causing said fluid-filled tube to vibrate and for sensing the frequency and amplitude of vibrations thus induced;
   a frequency meter for processing the output of said sensor means;
   a thermostat for maintaining said tube and said fluid at a selectable, constant temperature;
   a pump connected to, and arranged upstream of, said tube for moving said fluid through said tube at controllable rates of delivery;
   a flow resistance connectable to, and arranged downstream of, said tube to pressurize said fluid in dependence on said rates of delivery, and
   at least one fluid-containing bottle attachable to the suction line of said pump, further comprising a bypass valve arranged between said tube and said flow resistance, whereby flushing of said tube is accomplishable by opening said bypass valve to the atmosphere.

2. The densitometer as claimed in claim 1, further comprising a fluid-delivery system connectable to said suction line, for selectively delivering to said pump one at a time of a plurality of different fluid.

3. The densitometer as claimed in claim 1, wherein said device comprises three bottles selectively attachable to said suction line, a first bottle containing the fluid to be tested, a second bottle containing a first calibration fluid, and a third bottle containing a second calibration fluid, said calibration fluids serving for determinating a first and a second instrument constant.

4. The densitometer as claimed in claim 1, wherein said flow resistance is constituted by a tube filled with a finely grained substance.

5. The densitometer as claimed in claim 1, further comprising a control unit for controlling the rates of delivery of said pump.

6. A pressurized flow desitometer for the determination of the PVT properties of fluids conveyed by a pump having a suction valve, the densitometer comprising:

a tube through which the fluid to be tested flows;

exciter and sensor means for causing said fluid-filled tube to vibrate and for sensing the frequency and amplitude of vibrations thus induced;

a frequency meter for processing the output of said sensor means;

a thermostat for maintaining said tube and said fluid at a selectable, constant temperature;

a flow resistance connectable to, and arranged downstream of, said tube to pressurize said fluid at controllable rates of delivery; and at least one fluid-containing bottle attachable to the suction line of the pump and a bypass valve arranged between said tube and said flow resistance, whereby flushing of said tube is accomplished by opening said bypass valve to the atmosphere.

\* \* \* \* \*